United States Patent [19]

Brungraber

[11] Patent Number: 4,759,209

[45] Date of Patent: Jul. 26, 1988

[54] PORTABLE TESTER FOR MEASURING SLIP RESISTANCE

[76] Inventor: Robert J. Brungraber, 409 S. 21st St., Lewisburg, Pa. 17837

[21] Appl. No.: 60,302

[22] Filed: Jun. 10, 1987

[51] Int. Cl.<sup>4</sup> ............................................. G01N 19/02
[52] U.S. Cl. ............................................................ 73/9
[58] Field of Search ................................... 73/9, 10, 7

[56] References Cited

U.S. PATENT DOCUMENTS

| | | | |
|---|---|---|---|
| 2,225,140 | 12/1940 | Walker | 73/9 |
| 2,299,895 | 10/1942 | Harrali et al. | 73/9 |
| 2,955,455 | 10/1960 | Frederik | 73/9 |
| 3,098,377 | 7/1963 | Beauchamp | 73/9 |
| 3,187,552 | 6/1965 | Davies | 73/9 |
| 3,975,940 | 8/1976 | Brungraber | 73/9 |

OTHER PUBLICATIONS

Gough et al, *Journal of Scientific Instruments*, "A Simple Direct-reading friction meter", 30:345–349, Apr. 1953.

Primary Examiner—Stewart J. Levy
Assistant Examiner—Robert R. Raevis
Attorney, Agent, or Firm—Holman & Stern

[57] ABSTRACT

A portable apparatus for testing the slip resistance of surfaces such as floors and bathtub surfaces operates by applying a load instantaneously to a pad of friction material resting on the surface at a selected angle of attack. An articulated linkage carrying the pad is set at a predetermined angle and the load is substantially instantaneously applied to determine whether the pad slips at the preset angle. Tests may be successivley conducted at different angles of the linkage or a single go, no-go test may be conducted at a datum angle. The articulated linkage is carried on a pivoted frame which moves across a segment plate to establish the predetermined angle. A pawl and tooth type latching system holds the frame relative to the plate at the preset angle.

18 Claims, 4 Drawing Sheets

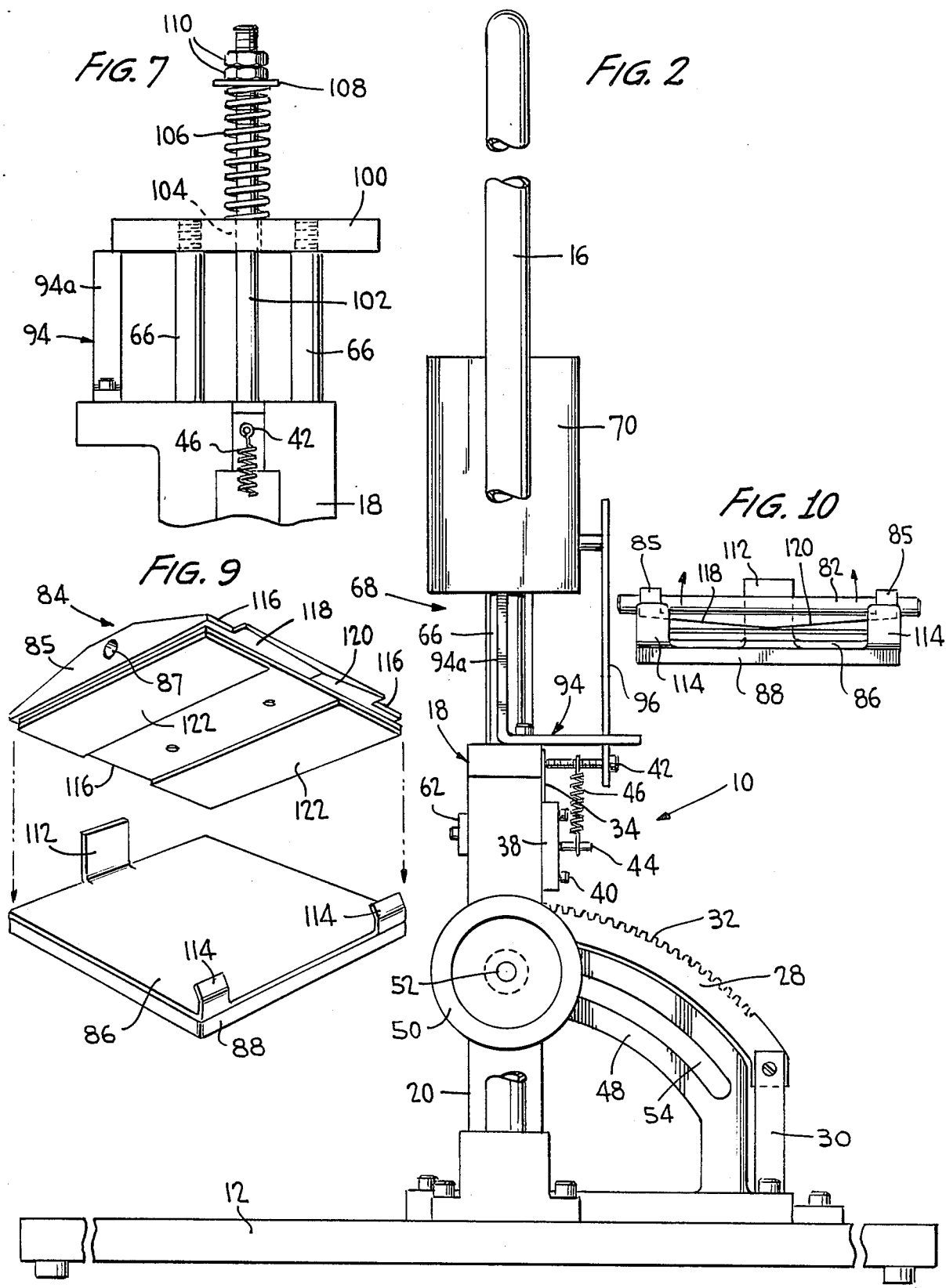

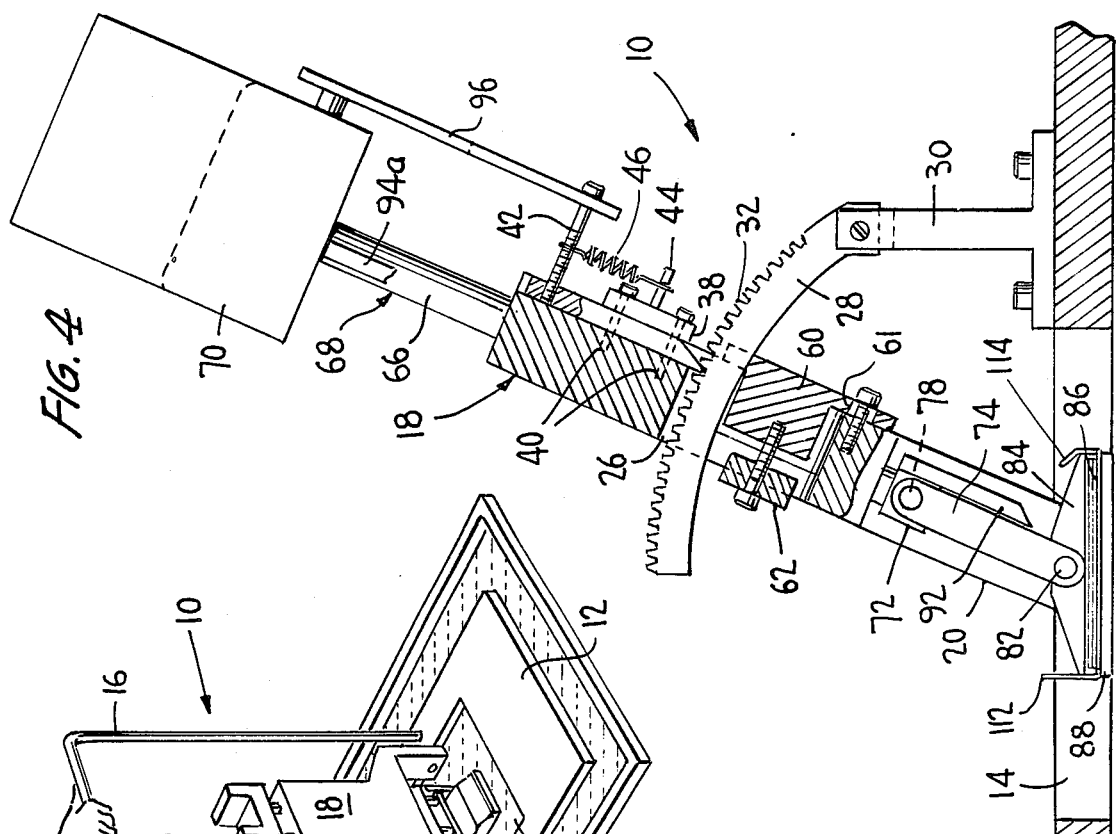

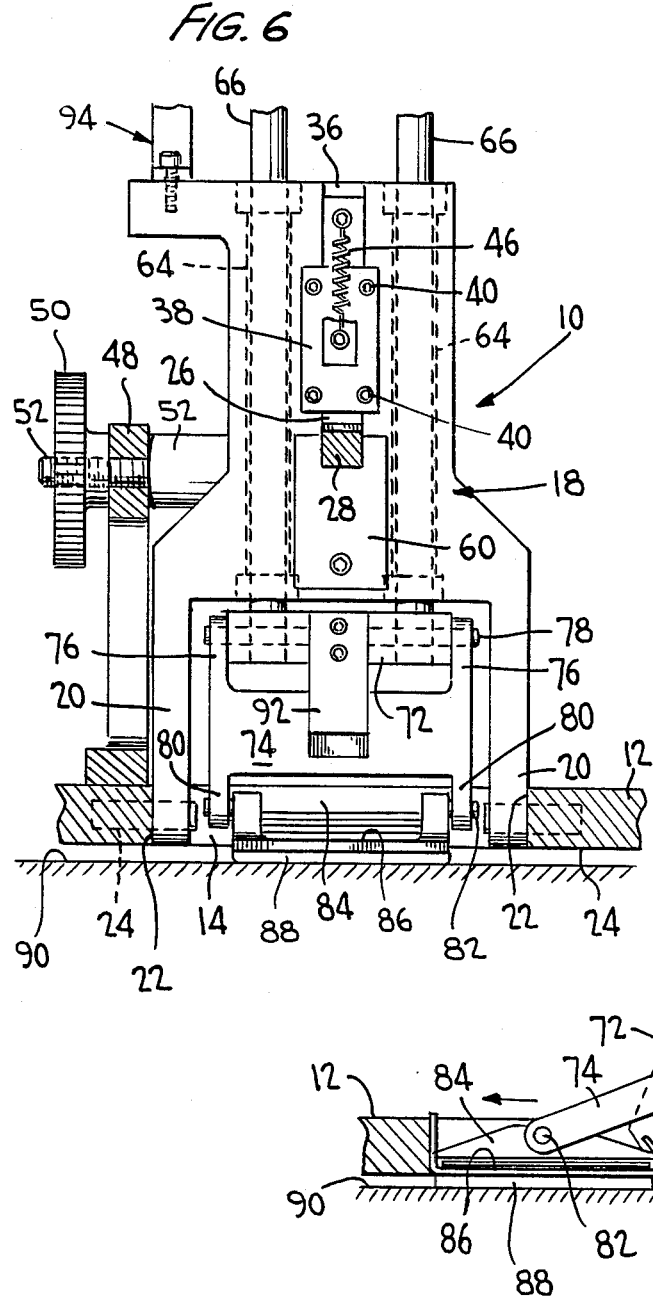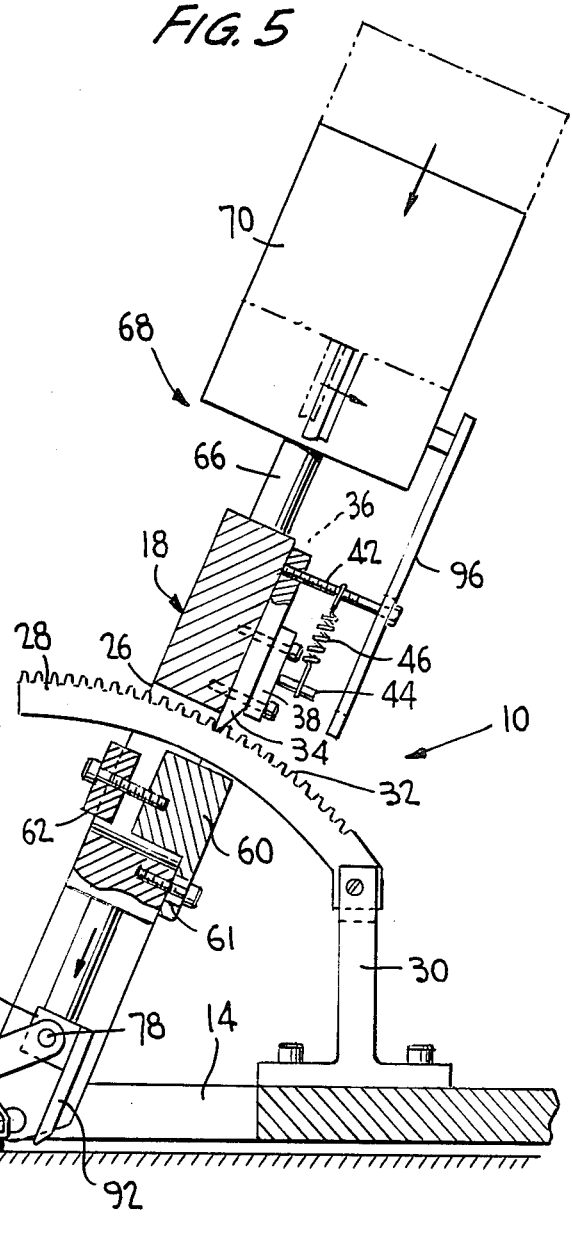

PORTABLE TESTER FOR MEASURING SLIP RESISTANCE

BACKGROUND OF THE INVENTION

This invention relates to apparatus for testing or measuring the slip resistance (static coefficient of friction) of surfaces such as floors, bathtubs and the like.

For example, industry standards are established for minimum friction coefficients that are acceptable in commercial flooring or bathtub interiors. In order to test such surfaces, these standards may be related, in the former case to the coefficient of friction as between the flooring surface and a material representative of a shoe sole, and the in the latter case to the coefficient of friction as between the bathtub surface and a material representative of human skin simulating the sole of the foot. Further, it is desirable for testing purposes, to have apparatus available which can be readily transported from site to site in order to test floor, bathtub and like surfaces for slip resistance, rather than having to submit a surface sample to a laboratory for testing.

Over the years, numerous different machines have been proposed for testing surface friction or slip resistance. The more successful of these, however, have often tended to be cumbersome making them unsuitable for in situ use. Applicant's prior U.S. Pat. No. 3,975,940, however, discloses a portable-type tester suitable for measuring the slip resistance of a surface on site, and which has been successfully used on a commercial basis for a number of years. Broadly stated, this apparatus consists of a box-like framework which is placed on a surface to be tested. The framework includes upper horizontal support rods on which a carriage element is mounted for horizontal sliding movement. The carriage supports a weighted vertical link which can slide up and down in the carriage. Another link is pivoted to the bottom of the weighted link and has a foot element at its lower end with a pad of friction material (e.g. shoe sole-simulating or human skin-simulating material) which rests on the surface being tested. When both links are in vertical alignment the force of the weight acts directly downwardly on the pad so that no slipping of the pad along the test surface can occur. However, the apparatus is further provided with springs which urge the carriage along the horizontal rods. This action continuously increases the angle between the links (since the pad is held by friction on the test surface) and gradually imposes a more and more angled force on the pad. Eventually, the force on the pad will be directed at a sufficiently shallow angle to cause the pad to slip on the test surface, the particular angle at which such slip takes place being representative of the friction coefficient of the test surface, and the machine includes a mechanism for registering the angle of slip.

Machines in accordance with the aforesaid patent, operate over a time frame for each test, constituted by the time taken for the carriage to move along the horizontal rods to the position at which the slip angle between the respective links is established. This mode of operation has been found to be generally satisfactory for most purposes, and the machine has been well accepted commercially. However, there is one situation in which it is felt that inconsistent results may be obtained, this being in the case of wet test surfaces. The inconsistencies in such situations may be attributable to the fact that in the time taken for the carriage to move along the horizontal rods from the vertical orientation of the links to the slip angle orientation, liquid may be forced out from between the pad and the test surface, so that a progressively drier or tackier interface results, giving a test reading which is not truly representative of the wet surface.

SUMMARY OF THE INVENTION

It is an object of the invention to provide a portable apparatus for testing the slip resistance of surfaces such as floors or bathtub surfaces, which overcomes, at least to a substantial extent, any possible inconsistencies resulting from wet test surfaces.

More particularly, it is an object of the invention to provide a portable test apparatus which includes an articulated linkage of a type similar to that used in the earlier patent and which has a foot plate with a pad of test material which rests on a surface to be tested, the apparatus including means for setting the linkage at selected angles and applying a load substantially instantaneously to the linkage at a selected angle to determine whether the pad will slip on the test at the selected angle.

In a preferred form of the invention, the apparatus includes an upright frame carrying the articulated linkage, the frame being pivotally mounted on a base and being supported for movement along a part-circular segment disposed in a vertical plane. The frame is movable along the segment into selected angles relative to the vertical so as to pre-establish an angle of attack for the articulated linkage relative to the test surface. To releasably fix the frame in the selected angular position on the segment, the segment may, for example, be toothed and the frame may have a sprung pawl to engage the teeth. A trigger mechanism may be provided between the frame and the articulated linkage to resist a downwardly applied load on the linkage until the trigger mechanism is released substantially instantaneously. The load may be applied by a weight or a spring.

By the above means, a load may be substantially instantaneously applied to the articulated linkage at a predetermined angle of attack. Only if the angle of attack is sufficiently shallow will the pad slip on the test surface. Thus, the machine may be used repeatedly to determine the angle of slip by trial and error, continually changing the angle, or a standard test angle of slip may be established as an acceptable datum for a particular surface to be tested. If the foot slips at the prescribed angle, the surface is more slippery than the prescribed standard, and if not, the surface is sufficiently slip resistant.

In another of its aspects, the invention provides a novel type of foot pad attachment for the articulated linkage of a slip testing apparatus as aforesaid, which provides for lateral tilting movements of the foot pad to accomodate surface irregularities and the like.

BRIEF DESCRIPTION OF THE DRAWINGS

FIG. 2 is a side elevational view of the tester, part broken away;

FIG. 3 is a sectional view, to a somewhat reduced scale, on line 3—3 of FIG. 1;

FIG. 4 is a view similar to FIG. 3 with the tester set at an operative angle ready for a test;

FIG. 5 is a view similar to FIG. 4 with the tester shown in a position assumed after a slip test;

FIG. 6 is a rear elevational view of part of the tester;

FIG. 7 is a rear elevational view of part of the tester showing a modification;

FIG. 8 is a perspective view of the tester showing one mode of use;

FIG. 9 is an exploded perspective view of a foot plate assembly; and

FIG. 10 is an elevational view of the foot plate assembly.

DESCRIPTION OF PREFERRED EMBODIMENTS

Figure 1:
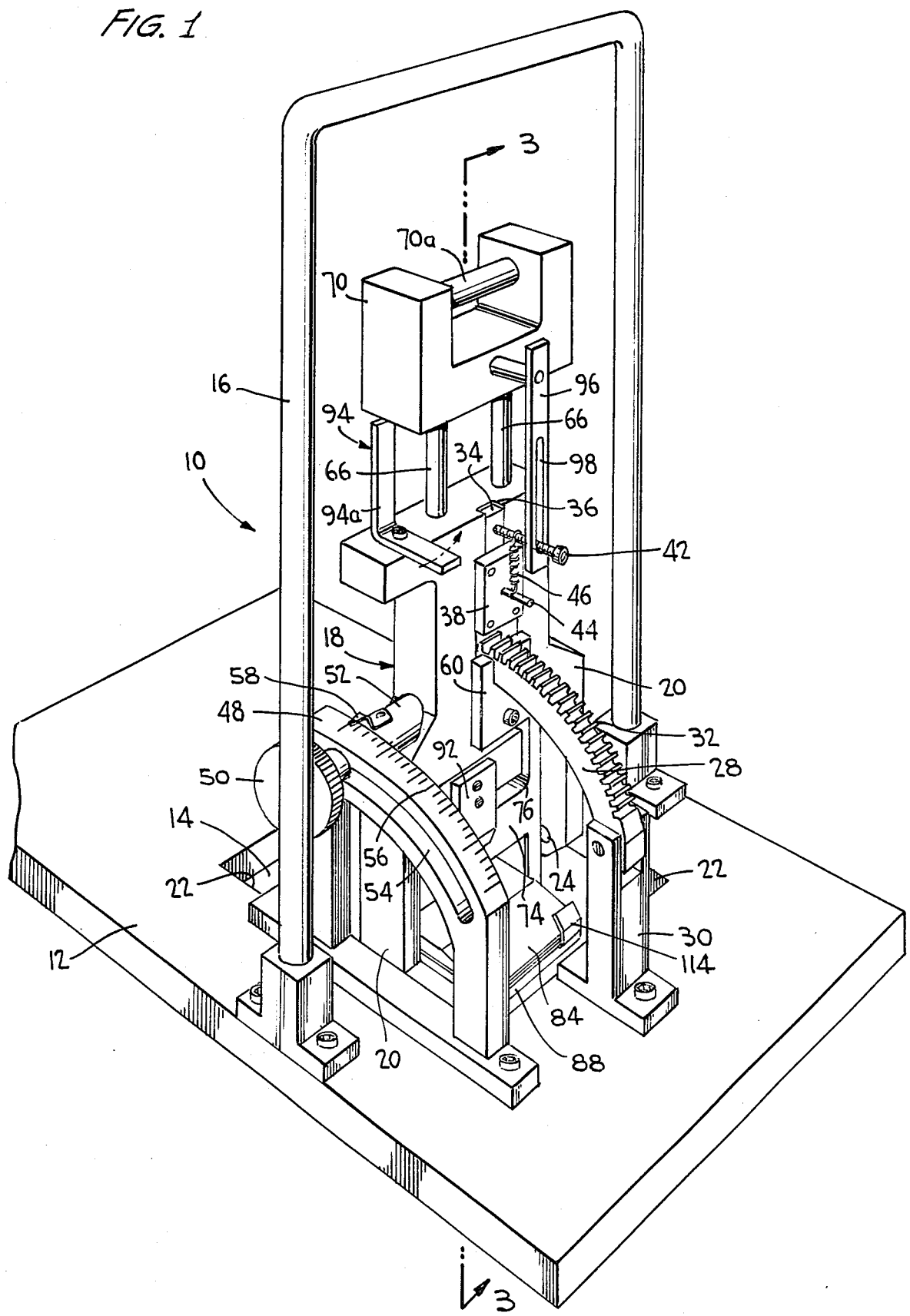
FIG. 1 is an overall perspective view of a portable tester for measuring slip resistance in accordance with a preferred embodiment of the invention.

The illustrated testing apparatus 10 has a planar support base 12 with a central aperture 14 and an elongate upstanding generally U-shaped carrying handle 16 spanning the aperture. An upright metal frame 18 has a yoke-like lower end with spaced limbs 20 (seen most clearly in FIG. 6), and the limbs 20 are pivotally attached at their lower ends to opposite lateral faces 22 of the base which define aperture 14, by pivot pins 24 so that frame 18 can swing as a whole about a horizontal axis defined by the pins.

Frame 18 has a substantially centrally located aperture 26 which received a part-circular segment plate 28 supported in a vertical plane, by an upright 30 secured to base 12 centrally of the aperture 14. The upper surface of the segment plate has teeth 32 to be engaged by a pawl 34 carried by frame 18. The pawl slides vertically in a slot 36 milled in the frame and covered by a plate 38 which is suitably secured to the frame as by screws 40. The pawl has a projecting pin 42, and plate 38 has a further pin 44. A coil spring 46 is attached between pins 42 and 44 so as to urge the pawl downwardly into latching engagement with the teeth 32. It will be readily apparent that by lifting pin 42 against the action of spring 46, the pawl can be disengaged from teeth 32, so that frame 18 can be swung about pivot pins 24 in order to set the frame at a required angle to the vertical (see for example FIGS. 3 and 4) and release of pin 42 will engage the pawl thereby releasably latching frame 18 at the set angle.

Also supported on the base 12, adjacent aperture 14, there may be provided a slotted segment 48, and frame 18 may be provided with a screw-down knob 50 on a lateral threaded pin 52 projecting through slot 54 of the segment, so as to more securely lock the frame 18 at a selected angle and prevent its movement, should the pawl be accidentally released. Segment 48 may have a measuring scale 56, which may be marked in degrees or other indicia such as slip coefficients, to determine the angular setting of frame 18, and the frame may have a corresponding scale pointer 58, see FIG. 1.

Frame 18 may be provided with a hardened steel or like bearing plate 60, with an adjustment slot 61, to embrace segment plate 28 and stabilize it laterally, and a front securement plate 62 for the bearing plate.

Frame 18 is further provided with a pair of laterally spaced vertical through-bores 64 (FIG. 6) containing a set of linear ball bushings (not shown) which may be counter sunk at their upper and lower ends, the bores 64 slidably receiving respective rods 66 which form part of an articulated linkage generally denoted by reference 68. At their upper ends, the rods 66 may be secured to a weight 70 and at their lower ends (which project downwardly into a space defined between the frame limbs 20) the rods may be secured to a cross-piece 72.

The weight 70, rods 66, and cross-piece 72 together define a first link of the articulated linkage 68.

Pivotally secured to cross-piece 72 is a yoke-like member 74 defining a second link of the articulated linkage. Upper limbs 76 of the member 74 may, for example, be journalled on a pivot pin 78 extending through the cross-piece. The member 74 may also have lower limbs 80 with a pivot pin 82 therebetween on which is pivotally mounted a foot-plate carrier 84. Pivotal mounting of the carrier on pin 82 is by way of sidewalls 85 on the carrier which have pin-receiving openings 87 (FIGS. 9 and 10). The foot-plate carrier has a foot plate 86 releasably secured thereto, as will be described, and the foot plate has an underneath pad 88 of test material (e.g. leather) which in use rests on a surface 90 to be tested within the aperture 14 of the base 12.

It is evident that the link member 74 can pivot in one direction relative to cross-piece 72 from a position in which member 74 is effectively in line with rods 66 (FIG. 3 or FIG. 4) to an out-of-line position (FIG. 5). However, member 74 is restrained from pivoting out-of-line with the rods in the other direction by a stop 92 secured to the cross-piece 72 and which engages member 74 in the in-line position.

In order to prevent the gravitational force of weight 70 and linkage 68 from acting through pad 88 on surface 90, until this force is required substantially instantaneously for test purposes, the apparatus is provided with a weight-supporting trigger in the form of an L-shaped lever 94 pivotally mounted atop frame 18. It will be evident that when the lever is in the position shown in FIG. 1, for example, its vertical limb 94a engages the weight and prevents if from applying pressure to pad 88. However, the lever can be readily swung out of engagement with the weight whereupon substantially instantaneous pressure will be applied to the pad.

When frame 18 is in a vertical position as shown in FIGS. 1 and 3, the force of weight 70 acts directly downwardly on pad 88, and effectively no slip can occur between the pad and surface 90. When, however, frame 18 is moved along segment plate 28 and latched at a particular angle, release of weight 70 causes a force with a horizontal component, the strength of which is dependent on the angle of frame 18, to act on pad 88. If the horizontal component of force is sufficient to overcome the friction between pad 88 and surface 90, the pad will slip and member 74 will swing to the position shown in FIG. 5. If, on the other hand, the angle at which frame 18 has been set is insufficiently removed from the vertical to apply a sufficiently large horizontal force component to pad 88 to cause slip, the apparatus will remain in the position shown in FIG. 4 even after the weight has been released. Accordingly, as previously indicated, slip tests may be conducted by trial and error, doing repeated tests at angles further and further removed from the vertical until the angle is reached at which slip occurs. Alternatively, a datum angle for frame 18 can be established for a particular surface, and a test can be conducted only at that angle to determine whether the surface is slip resistant or not at the specified angle. It is self evident that use of the device depends on a constant force being supplied by the weight at the various set angles of attack for accurate testing.

FIG. 8 shows one way of using the device, for example on a floor, where an operator will stabilize the device by standing on base 12 and gripping handle 16.

Alternatively, in a bathtub, for example, the device may be stabilized by two hands.

It will also be noted that weight 70 may include a handle bar 70a for raising the weight after a slip test. Further, the weight may carry a depending bar 96 with an elongate slot 98 which embraces the pawl-attached pin 42. Thus, raising of the weight may also be used to release the pawl, for repositioning the frame 18 on segment plate 28. When the weight falls, pin 42 moves along slot 98.

As an alternative to weight 70, force may be applied to pad 88 by a spring system as shown in FIG. 7. In this modification, the upper ends of rods 66 are secured to a further cross-piece 100, and a central rod 102 extends upwardly from the top of frame 18 to project through an aperture 104 in cross-piece 100. A coil spring 106 surrounds the projecting portion of rod 102 and acts between cross-piece 100 and a stop washer 108 or the like on rod 102 to exert downward force on the cross-piece and rods 66. As previously, L-shaped pivoting trigger 94 acts between the frame 18 and cross-piece 100 to resist the force of the spring until the trigger is released. Adjustment nuts 110 may be provided to alter the position of washer 108 on rod 102 and thereby adjust the force of the spring, if required.

FIGS. 9 and 10 show a preferred foot-plate construction in accordance with a further feature of the invention. It will be noted that foot-plate 86 has peripherally located upstanding tabs 112, 114 (tabs 114 being bent inwardly somewhat) and carrier 84 has corresponding locating slots 116 for receiving the tabs in a manner whereby the foot plate can be releasably clipped to the carrier. Magnetic strips 122 are provided to hold the foot plate 86 to the carrier 84. Also, the bottom of carrier 84 has a pair of inclined engagement surfaces 118, 120 front and back (only the engagement surfaces at the front of the carrier are shown in FIGS. 9 and 10) the surfaces defining apexes on an axis which is perpendicular to the axis of pivot pin 82 and which thereby allow the foot plate to tilt laterally to accommodate irregularities which may be present in test surface 90. Front to back tilting of the foot plate is provided by the pivotal mounting of carrier 84 on pivot pin 82. Replacement of foot plates, for example, to exchange pad 88 for one of a different composition, may easily be effected simply by unclipping the foot plate from the carrier.

While only preferred embodiments of the invention have been described herein in detail, the invention is not limited thereby and modifications can be made within the scope of the attached claims.

What is claimed is:

1. A portable apparatus for testing slip resistance of a surface comprising an articulated linkage having first and second pivotally interconnected links, a foot-plate carrier pivotally connected to the second link for supporting a foot-plate, having a pad of friction material, with the pad resting on a surface to be tested, support means for setting the first link at selected angles relative to the surface, and instantaneous force-applying means for selectively applying a downwardly directed load substantially instantaneously to the first link at selected angles of the first link to determine whether the pad will slip on the surface at a selected angle.

2. A portable apparatus for testing slip resistance of a surface comprising an articulated linkage having a foot-plate carrier for supporting a foot-plate, having a pad of friction material, with the pad resting on a surface to be tested, support means for setting the linkage at selected angles relative to the surface, and instantaneous force-applying means for selectively applying a downwardly directed load substantially instantaneously to the linkage at a selected angle of the linkage to determine whether the pad will slip on the surface at the selected angle, wherein the support means includes a base member for resting on the surface to be tested, an upright support frame pivotally secured to the base member for pivoting movements about a horizontal axis, the support frame slidably receiving the articulated linkage with the foot-plate carrier oriented for resting said pad on the surface, wherein the support means further includes an adjustment mechanism having cooperating components on the support frame and the base respectively for releasably setting the support frame at selected pivot angles relative to the base, and wherein the instantaneous force-applying means includes loading means for applying a downward force on the articulated linkage and releasable trigger means for preventing the loading means from applying said force until the trigger means is released.

3. Apparatus as defined in claim 2 wherein the adjustment mechanism includes a segment plate mounted on the base member, the segment plate being received in an aperture in said support frame, the support frame being movable along the segment plate for adjusting the angle of the support frame about said horizontal axis, and the cooperating components comprises engagable/disengagable latching means on the segment plate and support frame for releasably retaining the support frame in selected angular position relative to the segment plate.

4. Apparatus as defined in claim 3 wherein the latching means comprises peripheral teeth on the segment plate and a cooperable sprung pawl on the support frame for releasably engaging the teeth.

5. Apparatus as defined in claim 2 wherein the trigger means comprises a movable member insertable between the frame and the linkage for resisting the force of the loading means.

6. Apparatus as defined in claim 5 wherein the loading means is located atop a portion of the linkage projecting above the support frame and the removable member fits between an upper surface of the frame and a lower surface of the loading means.

7. Apparatus as defined in claim 6 wherein the removable member comprises an L-shaped lever having an horizontal limb pivotally mounted on the upper surface of the frame and a vertical limb engagable and disengagable with the lower surface of the loading means by pivotal movements of the lever.

8. Apparatus as defined in claim 6 wherein the loading means is a weight.

9. Apparatus as defined in claim 6 wherein the loading means comprises a spring assembly.

10. Apparatus as defined in claim 2 wherein the articulated linkage comprises rod means defining a first link slidably received in the support frame, with a lower end projecting from the frame, and a second link, pivotally connected to the lower end of the first link, the foot-plate carrier being pivotally connected to the second link.

11. Apparatus as defined in claim 10 wherein the second link is pivotal in one direction from an in-line orientation of the links, and the first link is provided with a stop member for preventing movement of the second link in an opposite direction from the in-line orientation of the links.

12. Apparatus as defined in claim 10 wherein the foot-plate carrier includes mounting means for releasably receiving a clip-on foot plate and friction pad assembly with provision for lateral swiveling movements of the foot plate and friction pad assembly on the carrier.

13. Apparatus defined in claim 12 wherein the mounting means includes peripheral slots on the carrier for receiving clip-on tabs on the foot plate and friction pad assembly, and mutually angled engagement surfaces on the carrier defining an apex for accomodating lateral swiveling movements of the foot plate and friction pad assembly.

14. A portable apparatus for testing slip resistance of a surface comprising a base member for resting on the surface, an upright frame mounted on the base member for pivoting movements about a substantially horizontal axis, adjustment means for releasably setting the frame at selected angles about said axis, an articulated linkage including a first link mounted for up and down movement on the frame and a second link pivotally connected to a lower end of the first link, a foot-plate carrier pivotally connected to the second link for supporting a foot plate friction pad with the pad resisting on said surface, and instantaneous force-applying means for selectively supplying a substantially instantaneous downwardly directed load on the first link with the frame set at a selected angle, to determine whether the pad will slip on the surface at the selected angle.

15. Apparatus as defined in claim 14 wherein the adjustment means comprises a segment plate supported on the base extending through an aperture in the frame with the frame being movable along the segment plate by pivotal movement of the frame about said axis, and interengagable latch means on the frame and segment plate respectively for releasably retaining the frame at a selected angular position along the segment plate.

16. Apparatus as defined in claim 14 wherein the base includes means defining an aperture and the frame is mounted on the base spanning the aperture with the foot plate carrier being positioned within the aperture.

17. Apparatus as defined in claim 14 wherein the first link has an upper portion projecting above the frame and the instantaneous force, applying means includes loading means on said upper portion of the first link and substantially instantaneously releasable trigger means insertable between the frame and the loading means for resisting the force of the loading means until the trigger means is released.

18. Apparatus as claimed in claim 14 including a clip-on foot plate and friction pad assembly connected to the foot plate carrier by means of a connection permitting lateral swiveling of the assembly.

* * * * *